United States Patent
Prasad et al.

(10) Patent No.: US 11,814,358 B2
(45) Date of Patent: Nov. 14, 2023

(54) PROCESS FOR THE PREPARATION OF 4-AMINO-N-TERT-BUTYL-4,5-DIHYDRO-3-ISOPROPYL-5-OXO-1H-1,2,4-TRIAZOLE-1-CARBOXAMIDE (AMICARBAZONE)

(71) Applicant: UPL LIMITED, Maharashtra (IN)

(72) Inventors: Vic Prasad, Mumbai (IN); Tinker McBrayer, New York, NY (US); Leandro Alves, Brazil (BR); Luiz Campos, Brazil (BR); Raj Arora, Mumbai (IN); Raj Tiwari, Mumbai (IN)

(73) Assignee: UPL LIMITED, Mumbai (IN)

( * ) Notice: Subject to any disclaimer, the term of this patent is extended or adjusted under 35 U.S.C. 154(b) by 0 days.

(21) Appl. No.: 17/401,269

(22) Filed: Aug. 12, 2021

(65) Prior Publication Data

US 2022/0177436 A1 Jun. 9, 2022

(30) Foreign Application Priority Data

Aug. 12, 2020 (IN) .............................. 202021034703

(51) Int. Cl.
C07D 249/12 (2006.01)
(52) U.S. Cl.
CPC .................................. C07D 249/12 (2013.01)
(58) Field of Classification Search
CPC ................................................... C07D 249/12
See application file for complete search history.

(56) References Cited

U.S. PATENT DOCUMENTS

| 5,708,184 | A | 1/1998 | Diehr |
| 9,332,762 | B2 | 5/2016 | Kim et al. |
| 2015/0336906 | A1* | 11/2015 | Kim ..................... C07D 249/12 560/159 |

FOREIGN PATENT DOCUMENTS

| CN | 107162933 A | 9/2017 |
| WO | 2014116012 A4 | 3/2015 |

OTHER PUBLICATIONS

Tert-Butyl isocyanate, 97%. Datasheet [online]. PubChem, available on Jul. 12, 2007 [retrieved on Feb. 4, 2023]. Retrieved from the Internet: <URL:https://pubchem.ncbi.nlm.nih.gov/substance/24848656>.*
No new references.*

* cited by examiner

*Primary Examiner* — Shawquia Jackson
(74) *Attorney, Agent, or Firm* — CANTOR COLBURN LLP

(57) ABSTRACT

The present invention relates to an improved process for the preparation of 4-amino-N-tert-butyl-4,5-dihydro-3-isopropyl-5-oxo-1H-1,2,4-triazole-1-carboxamide (Amicarbazone). The present invention more particularly relates to an improved process for the preparation of 4-amino-N-tert-butyl-4,5-dihydro-3-isopropyl-5-oxo-1H-1,2,4-triazole-1-carboxamide (Amicarbazone) by coupling of 4-Amino-2,4-dihydro-5-(1-methylethyl)-3H-1,2,4-triazol-3-one (TAZ) and poor quality tert-Butyl isocyanate (TBIC) with purity less than or equal to 98%, preferably less than or equal to 85%.

7 Claims, 6 Drawing Sheets

PROCESS FOR THE PREPARATION OF 4-AMINO-N-TERT-BUTYL-4,5-DIHYDRO-3-ISOPROPYL-5-OXO-1H-1,2,4-TRIAZOLE-1-CARBOXAMIDE (AMICARBAZONE)

FIELD OF THE INVENTION

The present invention relates to an improved process for the preparation of 4-amino-N-tert-butyl-4,5-dihydro-3-isopropyl-5-oxo-1H-1,2,4-triazole-1-carboxamide (Amicarbazone). The present invention more particularly relates to an improved process for the preparation of 4-amino-N-tert-butyl-4,5-dihydro-3-isopropyl-5-oxo-1H-1,2,4-triazole-1-carboxamide (Amicarbazone) by coupling of 4-Amino-2,4-dihydro-5-(1-methylethyl)-3H-1,2,4-triazol-3-one (TAZ) and poor quality tert-Butyl isocyanate (TBIC) with purity less than or equal to 85%, preferably less than or equal to 80%.

BACKGROUND OF THE INVENTION

Amicarbazone, 4-amino-N-tert-butyl-4,5-dihydro-3-isopropyl-5-oxo-1H-1,2,4-triazole-1-carboxamide is a member of the class of triazoles that is 4,5-dihydro-1H-1,2,4-triazol-5-one which is substituted at position 1 by a tert-butylaminocarbonyl group and at position 3 by an isopropyl group. Amicarbazone, is a triazolinone-based herbicidal active compound represented by Formula I.

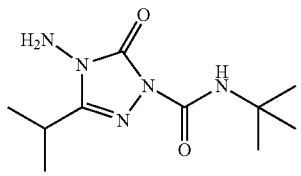

Formula I

4-Amino-2,4-dihydro-5-(1-methylethyl)-3H-1,2,4-triazol-3-one (TAZ) is represented by Formula II

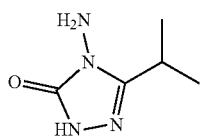

Formula II

Tert-Butyl isocyanate (TBIC) is represented by Formula III

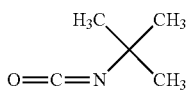

Formula III

The process for preparation of Amicarbazone by coupling of 4-Amino-2,4-dihydro-5-(1-methylethyl)-3H-1,2,4-triazol-3-one (TAZ) and tert-Butyl isocyanate (TBIC) is disclosed in U.S. Pat. No. 9,332,762(B2) (Indian equivalent 2071/KOLNP/2015).

U.S. Pat. No. 9,332,762(B2) (Indian equivalent 2071/KOLNP/2015) teaches process for preparation of Amicarbazone in example 10, 11 and 12 using amino-triazolinone (TAZ) and t-butyl isocyanate (TBIC). Further the process also involve the use of toluene and KOH.

Project pre-feasibility report for Proposed Expansion Project For Manufacturing of Agrochemical Active Ingredients & Intermediates and Fine Chemicals at Ankleshwar Project Proponent M/s. Deccan Fine Chemicals (India) Pvt. Ltd. (http://environmentclearance.nic.in/writereaddata/Online/TOR/03_May_2017_1900586535FXM3T5NAnnexure-Prefeasibilityreport.pdf)

This report teaches method Amicarbazone Preparation as follows,

Amicarbazone Preparation: TBIC and Triazolinone are charged into the reactor and heated less than 60° C. Tert-butylisocyanate is charged at a controlled rate at more than 65° C. After the completion of the reaction, mixture is neutralized and cooled.

Amicrabazone is isolated by filtration and then dried.

CN107162993A discloses synthesis of Amicarbazone by adding Triazolinones, potassium hydroxide, catalyst and the solvent into the reactor. Then the tertiary butyl isocyanates prepared is added dropwise, and a heating reaction is performed to obtain the amicarbazone.

Need of the Present Invention

The present inventors have observed that the production sites of Amicarbazone and site of origin of tert-Butyl isocyanate (TBIC) are generally different. At times, production sites may received poor quality (TBIC) which needs to be discarded. Tert-Butyl isocyanate may get decomposed either in transit to the production site or at the origin. Therefore, there is a need for development of a process capable of preparing Amicarbazone employing 4-Amino-2,4-dihydro-5-(1-methylethyl)-3H-1,2,4-triazol-3-one (TAZ) and poor quality tert-Butyl isocyanate (TBIC).

Solution Provided by the Present Invention

The present inventors have surprisingly developed a robust process to produce high quality active ingredient Amicarbazone with various grades of tertiary butyl isocyanate (TBIC).

The present inventors have found that with good quality tertiary butyl isocyanate (TBIC) it is routinely possible to produce high quality of active ingredient Amicarbazone. However, with tertiary butyl isocyanate (TBIC) of poor quality, only under modified conditions of the present invention it is possible to generate active ingredient meeting the approved specifications.

The present inventors found that tertiary butyl isocyanate (TBIC) of a lower grade can be utilized, via subtle process modifications, to generate Amicarbazone technical grade active ingredient meeting quality specifications.

The present invention provide a robust approach to generate acceptable quality (per manufacturing specifications.) Amicarbazone technical grade active ingredient via the use of poorer grade of TBIC which is hitherto unknown.

Advantages of the Present Invention

1. The present invention provide a versatile process that can utilize tertiary butyl isocyanate (TBIC) of poorer quality (low purity) to generate active ingredient Amicarbazone of high purity.

2. The present invention utilize tertiary butyl isocyanate (TBIC) of poorer quality (low purity) which would be generally discarded in case the same is decomposed for example TBIC, which is a highly reactive Isocyanate, needs to maintained/transported pure via exclusion of air/moisture and if not maintained it may decomposed during transit to production site. This would lower the cost of production of Amicarbazone.

OBJECTS OF THE INVENTION

It is an object of the present invention to provide a robust process to produce high quality active ingredient Amicarbazone with various grades of tertiary butyl isocyanate (TBIC) having low purity.

It is another object of the present invention to provide a process to produce high quality active ingredient, Amicarbazone with poor quality tert-Butyl isocyanate (TBIC) with purity equal to or less than 98%, preferably less than or equal to 85%.

SUMMARY OF THE INVENTION

According to an aspect of the present invention there is provided a process for the preparation of Amicarbazone comprising the step of:
i. Preparing a solution of 4-Amino-2,4-dihydro-5-(1-methylethyl)-3H-1,2,4-triazol-3-one (TAZ), Potassium hydroxide and toluene;
ii. Raising the temperature of the solution obtained in step (i) to the range of 50° C. to 70° C.;
iii. Adding tert-Butyl isocyanate (TBIC) without distillation to the solution of step (ii)
iv. Heating the solution obtained at temperature in the range of 60° C. to 75° C.;
v. Cooling the solution obtained in step (iv) to form Amicarbazone.

DETAILED DESCRIPTION OF THE INVENTION

The present invention relates to an improved process for the preparation of 4-amino-N-tert-butyl-4,5-dihydro-3-isopropyl-5-oxo-1H-1,2,4-triazole-1-carboxamide (Amicarbazone).

In an embodiment the present invention provide an improved process for the preparation of 4-amino-N-tert-butyl-4,5-dihydro-3-isopropyl-5-oxo-1H-1,2,4-triazole-1-carboxamide (Amicarbazone) by coupling of 4-Amino-2,4-dihydro-5-(1-methylethyl)-3H-1,2,4-triazol-3-one (TAZ) and poor quality tert-Butyl isocyanate (TBIC) with purity less than or equal to 88%, preferably less than or equal to 80%.

In another embodiment the present invention provide a process for the preparation of Amicarbazone comprising the step of:
i. Preparing a solution of 4-Amino-2,4-dihydro-5-(1-methylethyl)-3H-1,2,4-triazol-3-one (TAZ), Potassium hydroxide and toluene;
ii. Raising the temperature of the solution obtained in step (i) to the range of 50° C. to 70° C.;
iii. Adding tert-Butyl isocyanate (TBIC) without distillation to the solution of step (ii)
iv. Heating the solution obtained at temperature in the range of 60° C. to 75° C.;
v. Cooling the solution obtained in step (iv) to form Amicarbazone.

In the process of the present invention step (iii) comprises at least 18% molar excess of TBIC with respect to TAZ;

In the process of the present invention the solution is cooled to the temperature in the range of 40° C. to 50° C.;

In the process of the present invention the cooled solution is optionally seeded with Amicarbazone.

Poor quality tert-Butyl isocyanate (TBIC) is defined as a compound with purity less than or equal to 98%.

In an embodiment of the present invention the tert-Butyl isocyanate (TBIC) used in the process of the present invention have purity in the range of 80% to 98%.

In another embodiment of the present invention the tert ert-Butyl isocyanate (TBIC) used in the process of the present invention have purity less than 85%.

In yet another embodiment the present invention the Amicarbazone obtained as a final product have purity more than 97%.

In yet another embodiment the Heating, Cooling and Filtration may be carried out using conventional processes.

Figure 1:
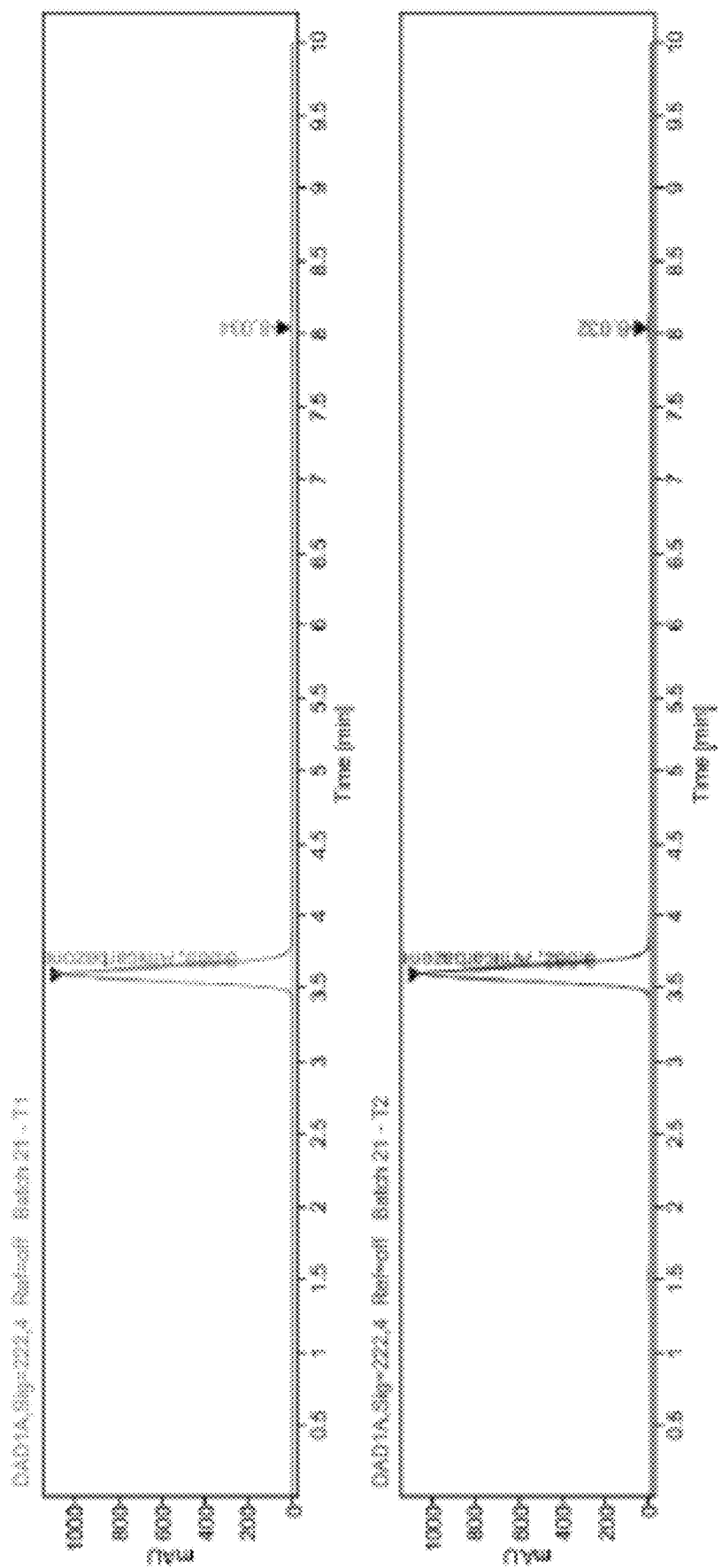
FIG. 1 show Amicarbazone purity (HPLC) achieved by the process of the present invention (Exp #21).
Figure 3:
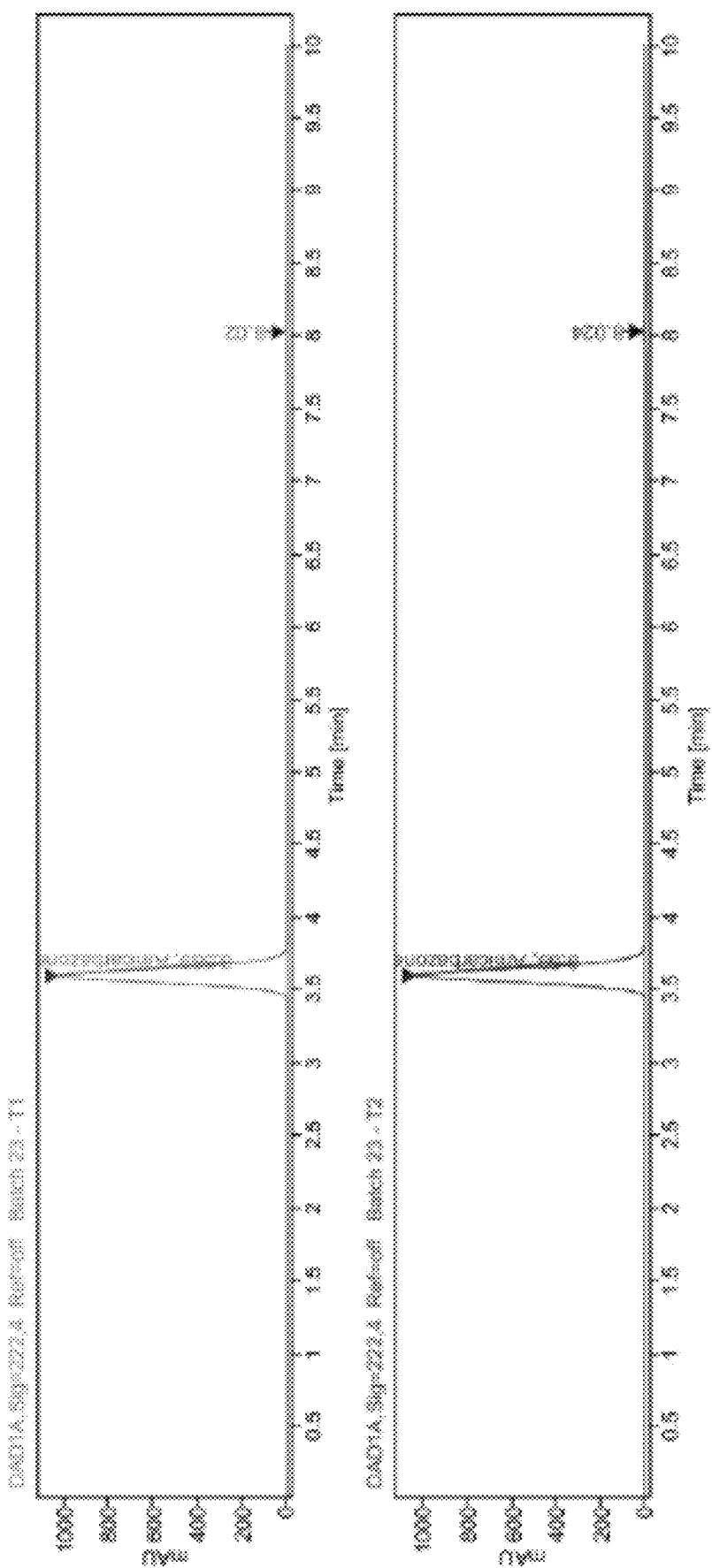
FIG. 3 show Amicarbazone purity (HPLC) achieved by the process of the present invention (Exp #23).
Figure 5:
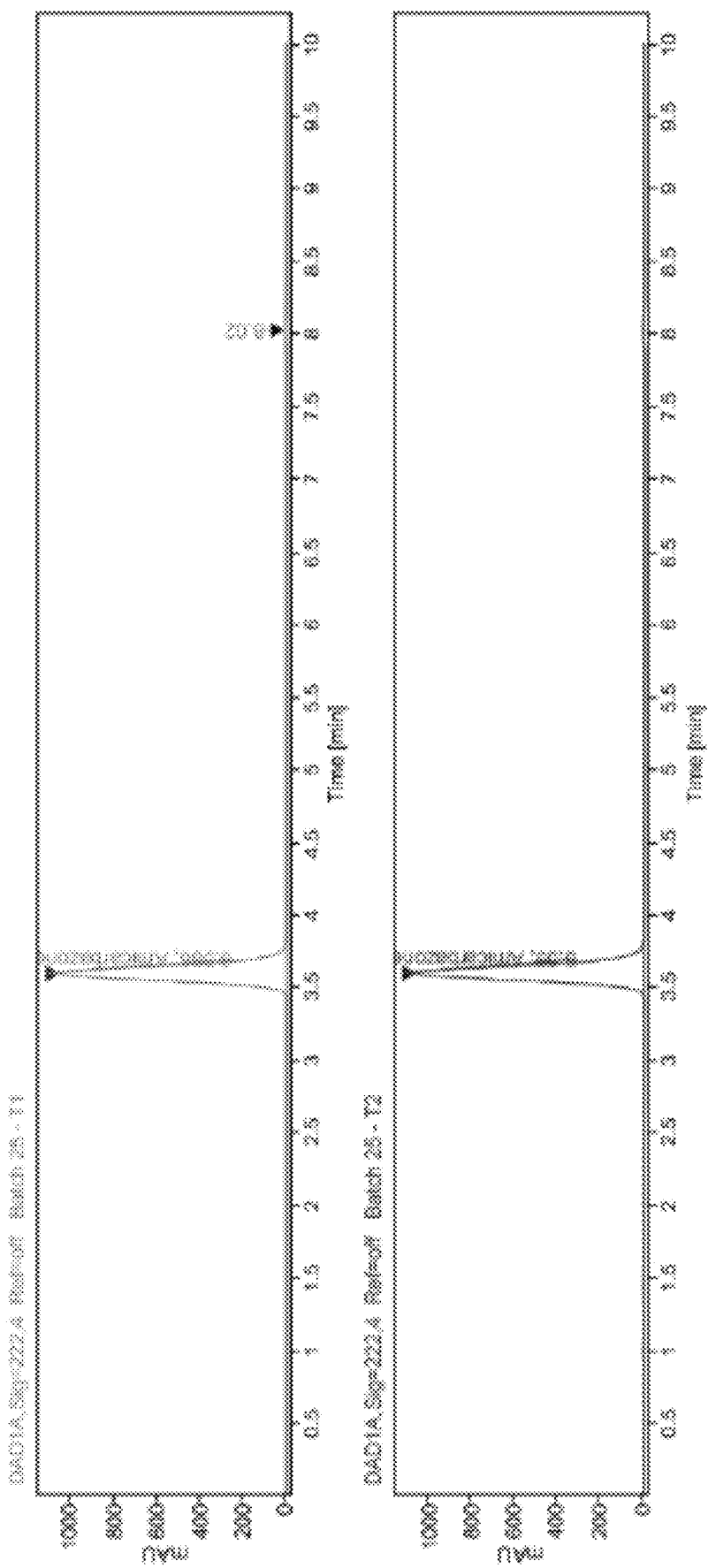
FIG. 5 show Amicarbazone purity (HPLC) achieved by the process of the present invention (Exp #25).

FIG. 1, FIG. 3 and FIG. 5 show Amicarbazone purity (HPLC) achieved according to coupling process of 4-Amino-2,4-dihydro-5-(1-methylethyl)-3H-1,2,4-triazol-3-one (TAZ) and poor quality tert-Butyl isocyanate (TBIC) with purity less than or equal to 80%, in order to get good quality of 4-amino-N-tert-butyl-4,5-dihydro-3-isopropyl-5-oxo-1H-1,2,4-triazole-1-carboxamide (Amicarbazone).

Figure 2:
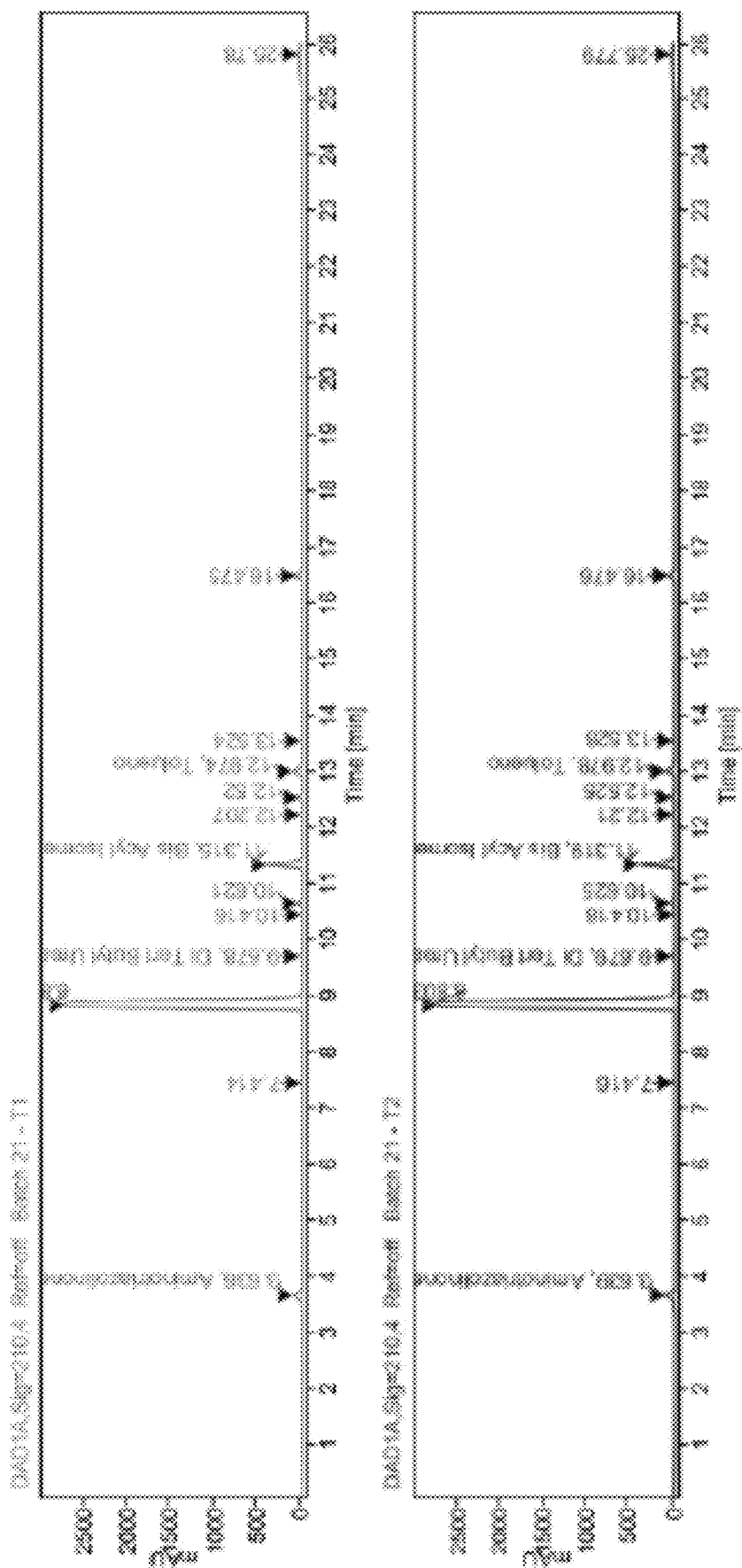
FIG. 2 show impurities (HPLC) detected in the Amicarbazone prepared by the process of the present invention (Exp #21).
Figure 4:
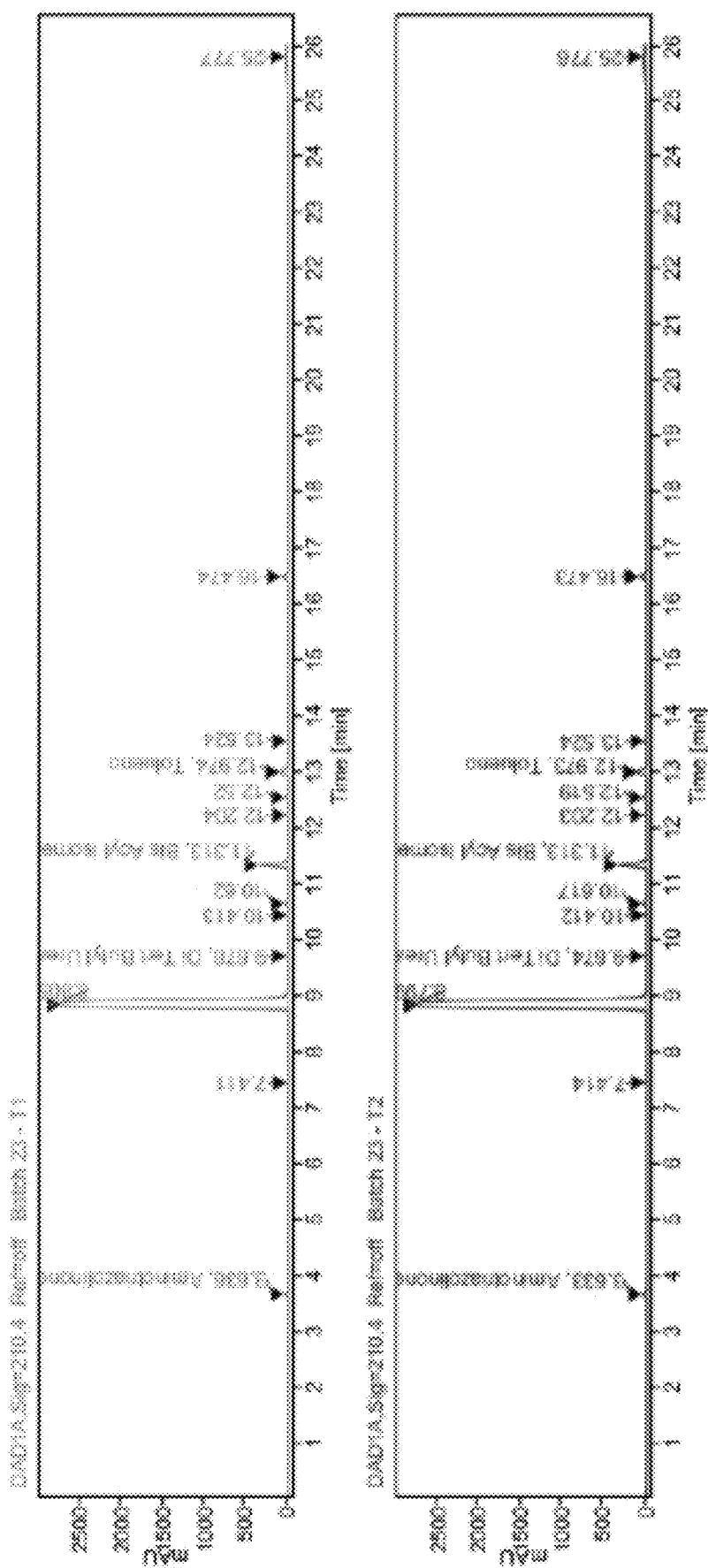
FIG. 4 show impurities (HPLC) detected in the Amicarbazone prepared by the process of the present invention (Exp #23).
Figure 6:
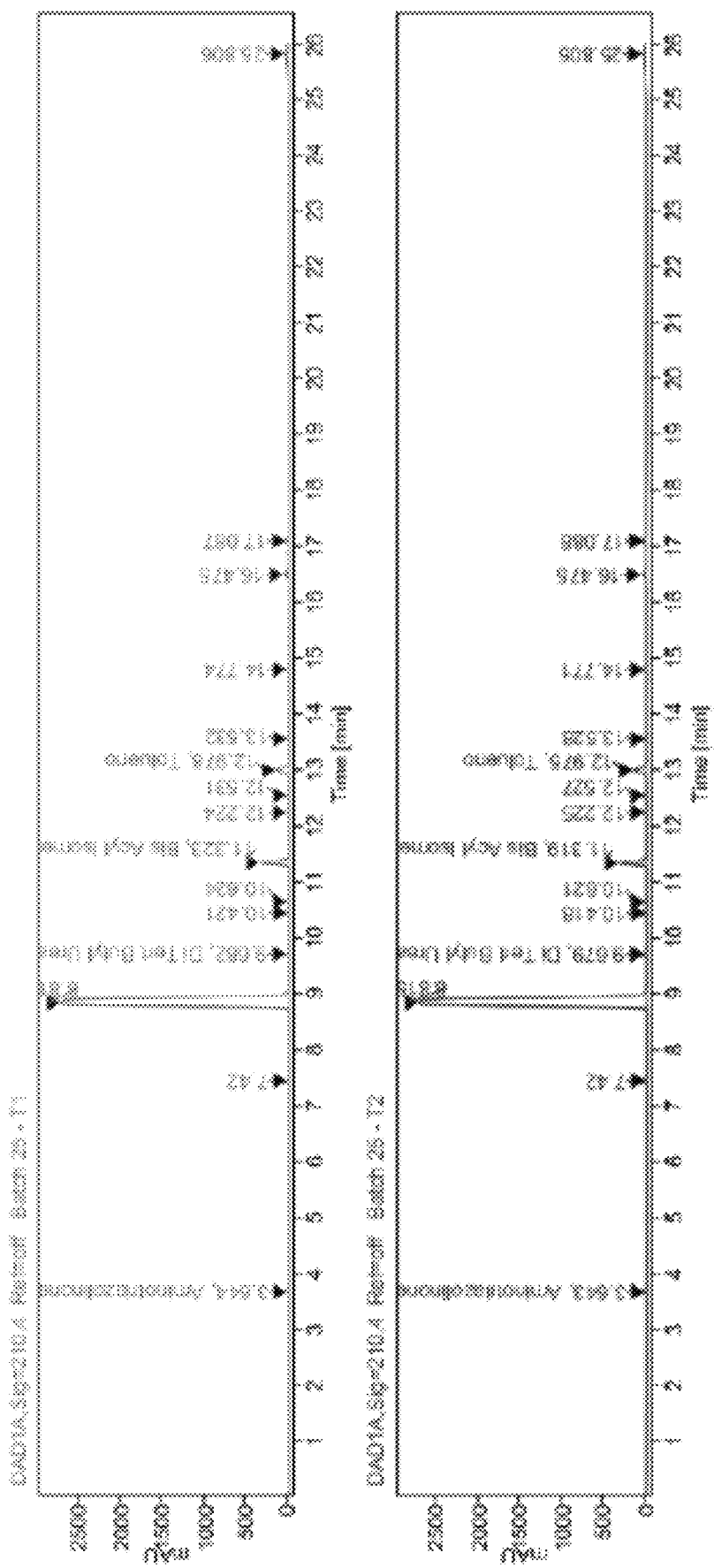
FIG. 6 show impurities (HPLC) detected in the Amicarbazone prepared by the process of the present invention (Exp #25).

FIG. 2, FIG. 4 and FIG. 6 show impurities (HPLC) detected in Amicarbazone when prepared by the process of the present invention.

The Results Achieved by Experiment 21 (FIGS. 1 and 2) are Tabulated in Table 1

TABLE 1

| Component | Specification | Result |
|---|---|---|
| Amicarbazone purity, % w/w | Minimum 96.5% | 97.3% |
| Bis-Acyl compound, % w/w | Maximum 1.30% | 1.16% |
| Di-tert-butil-urea, % w/w | Maximum 0.60% | 0.15% |
| 3H-1,2,4-triazol-3-one, 4 amino-2,4-dihydro-5-(1-methylethul), % w/w (Common name: Aminotriazolinone) | Maximum 0.40% | 0.48% |
| Toluene, % w/w | Maximum 0.50% | 0.11% |
| Karl Fischer, % ww | Maximum 0.30% | 0.14% |

The Results Achieved by Experiment 23 (FIGS. 3 and 4) are Tabulated in Table 2

TABLE 2

| Component | Specification | Result |
|---|---|---|
| Amicarbazone purity, % w/w | Minimum 96.5% | 97.4% |
| Bis-Acyl compound, % w/w | Maximum 1.30% | 0.97 |
| Di-tert-butil-urea, % w/w | Maximum 0.60% | 0.12 |
| 3H-1,2,4-triazol-3-one, 4 amino-2,4-dihydro-5-(1-methylethul), % w/w (Common name: Aminotriazolinone) | Maximum 0.40% | 0.18 |
| Toluene, % w/w | Maximum 0.50% | 0.11 |
| Karl Fischer, % ww | Maximum 0.30% | 0.20 |

The Results Achieved by Experiment 25 (FIGS. 5 and 6) are Tabulated in Table 3

TABLE 3

| Component | Specification | Result |
|---|---|---|
| Amicarbazone purity, % w/w | Minimum 96.5% | 98.2% |
| Bis-Acyl compound, % w/w | Maximum 1.30% | 0.93 |
| Di-tert-butil-urea, % w/w | Maximum 0.60% | 0.08 |
| 3H-1,2,4-triazol-3-one, 4 amino-2,4-dihydro-5-(1-methylethul), % w/w (Common name: Aminotriazolinone) | Maximum 0.40% | 0.02 |
| Toluene, % w/w | Maximum 0.50% | 0.17 |
| Karl Fischer, % ww | Maximum 0.30% | 0.08% |

Experiment 21, 23 and 25 are conducted in a manner as described in Example 1.

EXAMPLES

The present invention will now be explained in detail by reference to the following formulation examples and a test example, which should not be construed as limiting the scope of the present invention.

Example 1

Process for Preparation of 4-amino-N-tert-butyl-4,5-dihydro-3-isopropyl-5-oxo-1H-1,2,4-triazole-1-carboxamide (Amicarbazone) by Coupling of 4-Amino-2,4-dihydro-5-(1-methylethyl)-3H-1,2,4-triazol-3-one (TAZ) and Poor Quality tert-Butyl isocyanate (TBIC) with Purity Less than or Equal to 80%.
  i. Weight the required amount of Toluene, TAZ and Potassium hydroxide and put it under stirring into the 4-Neck Flask;
  ii. Drying (azeotropic drying (through the distillation column)) of TAZ under vacuum of 167 mmHg under controlled temperature between 61 to 67° C. until get the moisture level of 0.04% in the toluene;
  iii. Raise the temperature inside the flask and keep at 60° C. (±1° C.);
  iv. Increase agitation and add slowly and in constant flow in 30 minutes the required amount of TBIC undistilled in order to have 18% molar excess in relation to TAZ amount;
  v. Raise the temperature inside the flask slowly and in constantly heating to 70° C. (1° C.) in 10 min and keep it for 5 minutes;
  vi. Cool down the temperature slowly and in constantly inside the flask until 50° C. (1° C.) in 10 minutes and keep it;
  vii. Adding seed of Amicarbazone and keep stirring for 10 min;
  viii. Stop stirring and cool down the temperature inside the flask until 10° C. in 2 hours;
  ix. Filter the product formed and wash the crystals with the required amount of water;
  x. Dry the crystals under vacuum (200-400 mmHg) at 35-40° C. until get maximum 0.30% of moisture;
  xi. Assay the crystals using the specific method.

Example 2

Process for Preparation of 4-amino-N-tert-butyl-4,5-dihydro-3-isopropyl-5-oxo-1H-1,2,4-triazole-1-carboxamide (Amicarbazone) by Coupling of 4-Amino-2,4-dihydro-5-(1-methylethyl)-3H-1,2,4-triazol-3-one (TAZ) and Poor Quality tert-Butyl isocyanate (TBIC) with Purity Less than or Equal to 80%.
  i. 4-Amino-2,4-dihydro-5-(1-methylethyl)-3H-1,2,4-triazol-3-one (TAZ) and Potassium hydroxide solution drying under vacuum at 176 mmHg at 67° C.
  ii. Poor quality of tert-Butyl isocyanate (TBIC) without distillation adding under nitrogen atmosphere and controlled temperature of 60° C.;
  iii. Temperature raising until 70° C.;
  iv. Temperature cooling down until 50° C.;
  v. Add 4-amino-N-tert-butyl-4,5-dihydro-3-isopropyl-5-oxo-1H-1,2,4-triazole-1-carboxamide (Amicarbazone) seed;
  vi. Cooling down until 10° C. in 2 hours;
  vii. Filtration;
  viii. Drying under vacuum at 35-40° C.

The 4-amino-N-tert-butyl-4,5-dihydro-3-isopropyl-5-oxo-1H-1,2,4-triazole-1-carboxamide (Amicarbazone) purity and tert-Butyl isocyanate (TBIC) molar excess compared to 4-Amino-2,4-dihydro-5-(1-methylethyl)-3H-1,2,4-triazol-3-one (TAZ) are tabulated in Table 4.

TABLE 4

| Sr. Experiment No | Experiment No. | tert-Butyl isocyanate (TBIC) molar excess | 4-amino-N-tert-butyl-4,5-dihydro-3-isopropyl-5-oxo-1H-1,2,4-triazole-1-carboxamide (Amicarbazone) purity |
|---|---|---|---|
| 1 | Exp#25 | 18.00% | 98.20% |
| 2 | Exp#28 | 20.00% | 98.70% |
| 3 | Exp#29 | 22.00% | 98.40% |

Conclusion: The molar excess equal to or greater than 18.00% of Poor quality of tert-Butyl isocyanate (TBIC) compared to 4-Amino-2,4-dihydro-5-(1-methylethyl)-3H-1,2,4-triazol-3-one (TAZ) achieve high purity of 4-amino-N-tert-butyl-4,5-dihydro-3-isopropyl-5-oxo-1H-1,2,4-triazole-1-carboxamide (Amicarbazone).

Comparative Example 1

Process for Preparation of 4-amino-N-tert-butyl-4,5-dihydro-3-isopropyl-5-oxo-1H-1,2,4-triazole-1-carboxamide (Amicarbazone) by Coupling of 4-Amino-2,4-dihydro-5-(1-methylethyl)-3H-1,2,4-triazol-3-one (TAZ) and Poor Quality tert-Butyl isocyanate (TBIC) with Purity Less than or Equal to 80%.
  i. 4-Amino-2,4-dihydro-5-(1-methylethyl)-3H-1,2,4-triazol-3-one (TAZ) and Potassium hydroxide solution drying under vacuum at 176 mmHg at 67° C.
  ii. Poor quality of tert-Butyl isocyanate (TBIC) without distillation adding under nitrogen atmosphere and controlled temperature of 60° C.;
  iii. Temperature raising until 70° C.;
  iv. Temperature cooling down until 50° C.;
  v. Add 4-amino-N-tert-butyl-4,5-dihydro-3-isopropyl-5-oxo-1H-1,2,4-triazole-1-carboxamide (Amicarbazone) seed;
  vi. Cooling down until 10° C. in 2 hours;
  vii. Filtration;
  viii. Drying under vacuum at 35-40° C.

The 4-amino-N-tert-butyl-4,5-dihydro-3-isopropyl-5-oxo-1H-1,2,4-triazole-1-carboxamide (Amicarbazone) purity and tert-Butyl isocyanate (TBIC) molar excess compared to 4-Amino-2,4-dihydro-5-(1-methylethyl)-3H-1,2,4-triazol-3-one (TAZ) are tabulated in Table 5.

TABLE 5

| Sr. No | Experiment No. | tert-Butyl isocyanate (TBIC) molar excess | 4-amino-N-tert-butyl-4,5-dihydro-3-isopropyl-5-oxo-1H-1,2,4-triazole-1-carboxamide (Amicarbazone) purity |
|---|---|---|---|
| 1 | Exp#4 | 4.00% | 73.20% |
| 2 | Exp#6 | 9.50% | 83.50% |
| 3 | Exp#27 | 10.00% | 88.50% |

Conclusion: The molar excess less than 18.00% of poor quality of tert-Butyl isocyanate (TBIC) compared to 4-Amino-2,4-dihydro-5-(1-methylethyl)-3H-1,2,4-triazol-3-one (TAZ) achieve low purity of 4-amino-N-tert-butyl-4,5-dihydro-3-isopropyl-5-oxo-1H-1,2,4-triazole-1-carboxamide (Amicarbazone).

Comparative Example 2

Process for Preparation of 4-amino-N-tert-butyl-4,5-dihydro-3-isopropyl-5-oxo-1H-1,2,4-triazole-1-carboxamide (Amicarbazone) by Coupling of 4-Amino-2,4-dihydro-5-(1-methylethyl)-3H-1,2,4-triazol-3-one (TAZ) and Pure tert-Butyl isocyanate (TBIC) with Purity Higher than or Equal to 98%.
  i. 4-Amino-2,4-dihydro-5-(1-methylethyl)-3H-1,2,4-triazol-3-one (TAZ) and Potassium hydroxide solution drying under vacuum at 176 mmHg at 67° C.
  ii. Pure tert-Butyl isocyanate (TBIC) without distillation adding under nitrogen atmosphere and controlled temperature of 60° C.;
  iii. Temperature raising until 70° C.;
  iv. Temperature cooling down until 50° C.;
  v. Add 4-amino-N-tert-butyl-4,5-dihydro-3-isopropyl-5-oxo-1H-1,2,4-triazole-1-carboxamide (Amicarbazone) seed;
  vi. Cooling down until 10° C. in 2 hours;
  vii. Filtration;
  viii. Drying under vacuum at 35-40° C.

The 4-amino-N-tert-butyl-4,5-dihydro-3-isopropyl-5-oxo-1H-1,2,4-triazole-1-carboxamide (Amicarbazone) purity and tert-Butyl isocyanate (TBIC) molar excess compared to 4-Amino-2,4-dihydro-5-(1-methylethyl)-3H-1,2,4-triazol-3-one (TAZ) are tabulated in Table 6.

TABLE 6

| Sr. No | Experiment No. | tert-Butyl isocyanate (TBIC) molar excess | 4-amino-N-tert-butyl-4,5-dihydro-3-isopropyl-5-oxo-1H-1,2,4-triazole-1-carboxamide (Amicarbazone) purity |
|---|---|---|---|
| 1 | Exp#54 | 4.00% | 97.25% |
| 2 | Exp#60 | 3.00% | 98.27% |
| 3 | Exp#61 | 5.00% | 98.27% |

Conclusion: The molar excess less than 18.00% of Good quality of tert-Butyl isocyanate (TBIC) (i.e. 4-5% of TBIC molar excess) as compared to 4-Amino-2,4-dihydro-5-(1-methylethyl)-3H-1,2,4-triazol-3-one (TAZ) achieve high purity of 4-amino-N-tert-butyl-4,5-dihydro-3-isopropyl-5-oxo-1H-1,2,4-triazole-1-carboxamide (Amicarbazone).

Experimental Data

| Reactants | Purity (%) | B1 | B2 | B3 | B4 | B5 |
|---|---|---|---|---|---|---|
| TBIC (Poor quality) | 81.20% | 21.2923 | 21.2923 | 51.5728 | 51.5728 | 21.2936 |
| TBIC (Good quality) | 98.50% | -- | -- | -- | --- | -- |
| TAZ | 97.71% | 30 | 30 | 72.664 | 72.664 | 30 |
| Toluene | 99.27% | 103.6276 | 103.6276 | 300 | 251.8384 | 123.8577 |
| KOH (51.81%) | 51.81% | 0.4471 | 0.4471 | 1.0829 | 1.2995 | 0.6706 |
| Washing Water | -- | not measured | not measured | not measured | not measured | not measured |
| moles TBIC | | 0.215 | 0.215 | 0.520 | 0.520 | 0.215 |
| moles TAZ | | 0.206 | 0.206 | 0.500 | 0.500 | 0.206 |
| Moles Ratio TBIZ/TAZ | | 4.0% | 4.0% | 4.0% | 4.0% | 4.0% |
| TAZ | Azeotropic drying under vacuum? | No | No | No | No | No |
| TBIC adding | Was used TBIC distilled? | No | No | No | No | No |
| | Temperature inside the flask, ° C. | 60 | 60 | 60 | 60 | 60 |
| | Adding time, min | 15 | 15 | 15 | 15 | 21 |
| Molar excess of TBIC compared to TAZ | | 4.00% | 4.00% | 4.00% | 4.00% | 4.01% |
| Time kept at 70° C., min | | 10 | 10 | 10 | 10 | 22.5 |
| Time for cooling down until 50° C., min | | not measured | not measured | not measured | not measured | not measured |
| Time for cooling down at 10° C., min | | --- | --- | --- | --- | --- |

-continued

|  |  | Reagents | | | | |
|---|---|---|---|---|---|---|
| Reactants | Purity (%) | B1 | B2 | B3 | B4 | B5 |
| Amicarbazone purity, % w/w | | 17.0% | 62.0% | 49.8% | 73.0% | 55.2% |

Poor quality - TBIC = 81.20% purity
Azeotropic drying of TAZ under vacuum = No
Was used TBIC distilled = No
Molar excess of TBIC compared to TAZ = 4.00%
Amicarbazone purity, % w/w = Low purity

|  |  | Reagents | | | | |
|---|---|---|---|---|---|---|
| Reactants | Purity (%) | B6 | B7 | B8 | B9 | B10 |
| TBIC (Poor quality) | 81.20% | 38.68 | 34.105 | 22.33 | 22.977 | 22.4077 |
| TBIC (Good quality) | 98.50% | -- | -- | -- | --- | -- |
| TAZ | 97.71% | 51.7769 | 47.1471 | 29.8909 | 28.0572 | 29.9949 |
| Toluene | 99.27% | 137.3479 | 121.1027 | 79.2911 | 79.2911 | 79.567 |
| KOH (51.81%) | 51.81% | 0.9823 | 0.8661 | 0.5671 | 0.5835 | 0.5691 |
| Washing Water | -- | not measured | 41.3448 | 27.0702 | 27.0702 | not measured |
| moles TBIC | | 0.390 | 0.344 | 0.225 | 0.232 | 0.226 |
| moles TAZ | | 0.356 | 0.324 | 0.206 | 0.193 | 0.206 |
| Moles Ratio TBBI/TAZ | | 9.5% | 6.0% | 9.5% | 20.0% | 9.5% |
| TAZ | Azeotropic drying under vacuum? | Yes | Yes | Yes | Yes | Yes |
| TBIC adding | Was used TBIC distilled? | Yes | Yes | Yes | Yes | Yes |
|  | Temperature inside the flask, ° C. | 60 | 60 | 60 | 60 | 60 |
|  | Adding time, min | 30 | 30 | 30 | 30 | 30 |
| Molar excess of TBIC compared to TAZ | | 9.47% | 6.00% | 9.47% | 20.00% | 9.47% |
| Time kept at 70° C., min | | 30 | 5 | 5 | 5 | 5 |
| Time for cooling down until 50° C., min | | not measured | 30 | 15 | 10 | 10 |
| Time for cooling down at 10° C., min | | --- | 150 | 30 | 60 | 10 |
| Amicarbazone purity, % w/w | | 83.5% | 63.3% | 58.3% | 101.9% | 56.7% |

Poor quality - TBIC = 81.20% purity
Azeotropic drying under vacuum = Yes
Was used TBIC distilled = Yes
Molar excess of TBIC compared to TAZ = Less than 18%
Amicarbazone purity, % w/w = Low purity

|  |  | Reagents | | | | |
|---|---|---|---|---|---|---|
| Reactants | Purity (%) | B11 | B12 | B13 | B14 | B15 |
| TBIC (Poor quality) | 81.20% | 40.5817 | 47.7384 | 52.6735 | 55.4773 | 54.2132 |
| TBIC (Good quality) | 98.50% | -- | -- | -- | --- | -- |
| TAZ | 97.71% | 49.5542 | 58.2933 | 61.7467 | 65.0335 | 56.7425 |
| Toluene | 99.27% | 144.1006 | 169.5132 | 187.0371 | 196.9931 | 192.5044 |
| KOH | | | | | | |

-continued

|  |  | Reagents | | | | |
|---|---|---|---|---|---|---|
| Reactants | Purity (%) | B11 | B12 | B13 | B14 | B15 |
| (51.81%) | 51.81% | 1.0306 | 1.2124 | 1.3377 | 1.4089 | 1.3768 |
| Washing Water | -- | 27.0702 | 57.8723 | 63.8551 | 67.2541 | 65.7216 |
| moles TBIC | | 0.409 | 0.481 | 0.531 | 0.559 | 0.547 |
| moles TAZ | | 0.341 | 0.401 | 0.425 | 0.447 | 0.390 |
| Moles Ratio TBIZ/TAZ | | 20.0% | 20.0% | 25.0% | 25.0% | 40.0% |
| TAZ | Azeotropic drying under vacuum? | Yes | Yes | Yes | Yes | Yes |
| TBIC adding | Was used TBIC distilled? | Yes | Yes | No | No | No |
| | Temperature inside the flask, °C. | 60 | 60 | 60 | 60 | 60 |
| | Adding time, mm | 30 | 30 | 30 | 30 | 30 |
| Molar excess of TBIC compared to TAZ | | 20.00% | 20.00% | 25.00% | 25.00% | 40.00% |
| Time kept at 70° C., min | | 5 | 5 | 5 | 5 | 5 |
| Time for cooling down until 50° C., min | | 10 | 10 | 10 | 10 | 10 |
| Time for cooling down at 10° C., min | | 60 | 60 | 60 | 60 | 60 |
| Amicarbazone purity, % w/w | | 90.0% | 82.2% | 97.5% | 92.7% | 92.2% |

Poor quality - TBIC = 81.20% purity
Azeotropic drying under vacuum = Yes
Was used TBIC distilled = No
Molar excess of TBIC compared to TAZ = More than 18%
Amicarbazone purity, % w/w = high purity

|  |  | Reagents | | | | |
|---|---|---|---|---|---|---|
| Reactants | Purity (%) | B16 | B17 | B18 | B19 | B20 |
| TBIC (Poor quality) | 81.20% | 55.7794 | 55.4773 | 55.681 | 55.6993 | 64.1688 |
| TBIC (Good quality) | 98.50% | -- | -- | -- | --- | -- |
| TAZ | 97.71% | 62.8727 | 65.0335 | 67.9919 | 68.0143 | 78.3564 |
| Toluene | 99.27% | 198.0658 | 196.9931 | 197.7164 | 197.7814 | 227.8555 |
| KOH (51.81%) | 51.81% | 1.4874 | 1.4089 | 1.4848 | 1.4853 | 1.7111 |
| Washing Water | -- | 68.6203 | 67.2541 | 67.501 | 67.5232 | 77.7906 |
| moles TBIC | | 0.562 | 0.559 | 0.561 | 0.562 | 0.647 |
| moles TAZ | | 0.433 | 0.447 | 0.468 | 0.468 | 0.539 |
| Moles Ratio TBIZ/TAZ | | 30.0% | 25.0% | 20.0% | 20.0% | 20.0% |
| TAZ | Azeotropic drying under vacuum? | Yes | Yes | Yes | Yes | Yes |
| TBIC adding | Was used TBIC distilled? | No | No | No | No | No |
| | Temperature inside the flask, °C. | 60 | 60 | 60 | 60 | 60 |
| | Adding time, min | 30 | 30 | 30 | 30 | 30 |
| Molar excess of TBIC compared to TAZ | | 30.00% | 25.00% | 20.00% | 20.00% | 20.00% |
| Time kept at 70° C., min | | 5 | 5 | 5 | 5 | 5 |

-continued

|  |  | Reagents | | | | |
|---|---|---|---|---|---|---|
| Reactants | Purity (%) | B16 | B17 | B18 | B19 | B20 |
| Time for cooling down until 50° C., min | | 10 | 10 | 10 | 10 | 10 |
| Time for cooling down at 10° C., min | | 60 | 60 | 120 | 120 | 120 |
| Amicarbazone purity, % w/w | | 88.1% | 98.0% | 99.7% | 99.4% | 98.1% |

Poor quality - TBIC = 81.20% purity
Azeotropic drying of TAZ under vacuum = Yes
Was used TBIC distilled = No
Molar excess of TBIC compared to TAZ = More than 18%
Amicarbazone purity, % w/w = high purity

|  |  | Reagents | | | | |
|---|---|---|---|---|---|---|
| Reactants | Purity (%) | B21 | B22 | B23 | B24 | B25 |
| TBIC (Poor quality) | 81.20% | 200.0000 | 64.1688 | 350.0000 | 300.0000 | 300.0000 |
| TBIC (Good quality) | 98.50% | -- | -- | -- | --- | -- |
| TAZ | 97.71% | 244.2196 | 78.3564 | 427.3842 | 366.3293 | 372.4959 |
| Toluene | 99.27% | 710.1754 | 227.8555 | 1242.807 | 1065.2632 | 1065.2632 |
| KOH (51.81%) | 51.81% | 5.3333 | 1.7111 | 9.332 | 7.9999 | 7.9999 |
| Washing Water | -- | 242.4561 | 77.7906 | 424.2982 | 363.6842 | 363.6842 |
| moles TBIC | | 2.017 | 0.647 | 3.529 | 3.025 | 3.025 |
| moles TAZ | | 1.680 | 0.539 | 2.941 | 2.521 | 2.563 |
| Moles Ratio TBIZ/TAZ | | 20.0% | 20.0% | 20.0% | 20.0% | 18.0% |
| TAZ | Azeotropic drying under vacuum? | Yes | Yes | Yes | Yes | Yes |
| TBIC adding | Was used TBIC distilled? | No | No | No | No | No |
| | Temperature inside the flask, ° C. | 60 | 60 | 60 | 60 | 60 |
| | Adding time, min | 30 | 30 | 30 | 30 | 30 |
| Molar excess of TBIC compared to TAZ | | 20.00% | 20.00% | 20.00% | 20.00% | 18.01% |
| Time kept at 70° C., min | | 5 | 5 | 5 | 5 | 5 |
| Time for cooling down until 50° C., min | | 10 | 10 | 10 | 10 | 10 |
| Time for cooling down at 10° C., min | | 120 | 120 | 120 | 120 | 120 |
| Amicarbazone purity, % w/w | | 97.3% | 97.2% | 97.4% | 97.8% | 98.2% |

Poor quality - TBIC = 81.20% purity
Azeotropic drying of TAZ under vacuum = Yes
Was used TBIC distilled = No
Molar excess of TBIC compared to TAZ = More than 18%
Amicarbazone purity, % w/w = high purity

|  |  | Reagents | | | | |
|---|---|---|---|---|---|---|
| Reactants | Purity (%) | B26 | B27 | B28 | B29 | B30 |
| TBIC (Poor quality) | 81.20% | 65.0000 | 62.1739 | 350.0000 | 350.0000 | 350.0000 |
| TBIC (Good quality) | 98.50% | -- | -- | -- | --- | -- |
| TAZ | 97.71% | 82.8223 | 82.8223 | 427.3842 | 420.332398 | 420.3324 |
| Toluene | 99.27% | 230.8070 | 230.8070 | 1242.807 | 1242.807 | 1242.807 |

-continued

|  |  | Reagents | | | | |
| --- | --- | --- | --- | --- | --- | --- |
| Reactants | Purity (%) | B26 | B27 | B28 | B29 | B30 |
| KOH (51.81%) | 51.81% | 1.7333 | 1.7333 | 9.332 | 9.4506 | 9.4506 |
| Washing Water | -- | 78.7982 | 78.7982 | 424.2982 | 424.2982 | 424.2982 |
| moles TBIC |  | 0.655 | 0.627 | 3.529 | 3.529 | 3.529 |
| moles TAZ |  | 0.570 | 0.570 | 2.941 | 2.892 | 2.892 |
| Moles Ratio TBIZ/TAZ |  | 15.0% | 10.0% | 20.0% | 22.0% | 22.0% |
| TAZ | Azeotropic drying under vacuum? | Yes | Yes | Yes | Yes | Yes |
| TBIC adding | Was used TBIC distilled? | No | No | No | No | No |
|  | Temperature inside the flask, °C. | 60 | 60 | 60 | 60 | 60 |
|  | Adding time, min | 30 | 30 | 30 | 30 | 30 |
| Molar excess of TBIC compared to TAZ |  | 15.00% | 10.00% | 20.00% | 22.01% | 22.01% |
| Time kept at 70° C., min |  | 5 | 5 | 5 | 5 | 5 |
| Time for cooling down until 50° C., min |  | 10 | 10 | 10 | 10 | 10 |
| Time for cooling down at 10° C., min |  | 120 | 120 | 120 | 120 | 120 |
| Amicarbazone purity, % w/w |  | 88.5% | 88.5% | 98.7% | 97.8% | 97.7% |

Poor quality - TBIC = 81.20% purity  
Azeotropic drying of TAZ under vacuum = Yes  
Was used TBIC distilled = No  
Molar excess of TBIC compared to TAZ = More than 18%  
Amicarbazone purity, % w/w = high purity

|  |  | Reagents | | | | |
| --- | --- | --- | --- | --- | --- | --- |
| Reactants | Purity (%) | B31 | B32 | B33 | B34 | B35 |
| TBIC (Poor quality) | 81.20% | 350.0000 | 350.0000 | 350.0000 | 116.6667 | 116.6667 |
| TBIC (Good quality) | 98.50% |  |  |  |  |  |
| TAZ | 97.71% | 420.3324 | 420.3324 | 427.3842 | 142.4614 | 140.1108 |
| Toluene | 99.27% | 1242.807 | 1242.807 | 1242.807 | 414.2690 | 414.2690 |
| KOH (51.81%) | 51.81% | 9.4506 | 9.4506 | 9.4506 | 3.1502 | 3.1502 |
| Washing Water | -- | 424.2982 | 424.2982 | 424.2982 | 141.4327 | 141.4327 |
| moles TBIC |  | 3.529 | 3.529 | 3.529 | 1.176 | 1.176 |
| moles TAZ |  | 2.892 | 2.892 | 2.941 | 0.980 | 0.964 |
| Moles Ratio TBIZ/TAZ |  | 22.0% | 22.0% | 20.0% | 20.0% | 22.0% |
| TAZ | Azeotropic drying under vacuum? | Yes | Yes | Yes | Yes | Yes |
| TBIC adding | Was used TBIC distilled? | No | No | No | No | No |
|  | Temperature inside the flask, °C. | 60 | 60 | 60 | 60 | 60 |
|  | Adding time, min | 30 | 30 | 30 | 30 | 30 |
| Molar excess of TBIC compared to TAZ |  | 22.01% | 22.01% | 20.00% | 20.00% | 22.01% |
| Time kept at 70° C., min |  | 5 | 5 | 5 | 5 | 5 |
| Time for cooling down until 50° C., min |  | 10 | 10 | 10 | 10 | 10 |
| Time for cooling down at 10° C., min |  | 120 | 120 | 120 | 120 | 120 |

|  |  | Reagents |  |  |  |  |
|---|---|---|---|---|---|---|
| Reactants | Purity (%) | B31 | B32 | B33 | B34 | B35 |
| Amicarbazone purity, % w/w |  | 90.4% | 90.7% | 93.5% | 91.6% | 92.6% |

Poor quality - TBIC = 81.20% purity
Azeotropic drying of TAZ under vacuum = Yes
Was used TBIC distilled = No
Molar excess of TBIC compared to TAZ = More than 18%
Amicarbazone purity, % w/w = high purity

| Reagents | Purity (%) |  | Reactants |  |  |  |
|---|---|---|---|---|---|---|
|  |  |  | B37 | B38 | B39 | B40 |
| TBIC (Poor quality) | 81.20% |  | 116.6667 | 115.7398 | 86.8049 | 86.8049 |
| TBIC (Good quality) | 98.50% |  |  |  |  |  |
| TAZ | 97.71% |  | 135.6764 | 135.6764 | 104.2239 | 115.6264 |
| Toluene | 99.27% |  | 414.2690 | 414.2690 | 310.7018 | 310.7018 |
| KOH (51.81%) | 51.81% |  | 3.1502 | 3.1502 | 2.3626 | 2.3626 |
| Washing Water | — |  | 141.4327 | 141.4327 | 106.0746 | 106.0746 |
| moles TBIC |  |  | 1.176 | 1.167 | 0.875 | 0.875 |
| moles TAZ |  |  | 0.934 | 0.934 | 0.717 | 0.796 |
| Moles Ratio TBIZ/TAZ |  |  | 26.0% | 25.0% | 22.0% | 10.0% |
| TAZ |  | Azeotropic drying under vacuum? | Yes | Yes | Yes | Yes |
| TBIC adding |  | Was used TBIC distilled? | No | No | No | No |
|  |  | Temperature inside the flask, ° C. | 60 | 60 | 60 | 60 |
|  |  | Adding time, min | 30 | 30 | 30 | 30 |
| Molar excess of TBIC compared to TAZ |  |  | 26.00% | 25.00% | 22.04% | 10.01% |
| Time kept at 70° C., min |  |  | 5 | 5 | 5 | 5 |
| Time for cooling down until 50° C., min |  |  | 10 | 10 | 10 | 10 |
| Time for cooling down at 10° C., min |  |  | 120 | 120 | 120 | 120 |
| Amicarbazone purity, % w/w |  |  | 97.6% | 90.8% | 92.9% | 89.6% |

Poor quality - TBIC = 81.20% purity
Azeotropic drying of TAZ under vacuum = Yes
Was used TBIC distilled = No
Molar excess of TBIC compared to TAZ = More than 18%
Amicarbazone purity, % w/w = high purity

|  |  | Reagents |  |  |  |  |
|---|---|---|---|---|---|---|
| Reactants | Purity (%) | B41 | B42 | B43 | B44 | B45 |
| TBIC (Poor quality) | 81.20% | 26.6154 | 212.9231 | 26.6154 | 26.6154 | 29.1667 |
| TBIC (Good quality) | 98.50% | -- | -- | -- | -- | -- |
| TAZ | 97.71% | 30.0000 | 240.0000 | 30.4699 | 29.3242 | 35.0277 |
| Toluene | 99.27% | 95.2648 | 762.1183 | 95.2648 | 95.2648 | 103.5673 |
| KOH (51.81%) | 51.81% | 0.7244 | 5.7953 | 0.7244 | 0.7244 | 0.7875 |
| Washing Water | -- | 32.5237 | 260.1896 | 32.5237 | 32.5237 | 35.3582 |
| moles TBIC |  | 0.268 | 2.147 | 0.268 | 0.268 | 0.294 |
| moles TAZ |  | 0.206 | 1.651 | 0.210 | 0.202 | 0.241 |
| Moles Ratio TBIZ/TAZ |  | 30.00% | 30.00% | 28.00% | 33.00% | 22.01% |

|  |  | Reagents |  |  |  |  |
|---|---|---|---|---|---|---|
| Reactants | Purity (%) | B41 | B42 | B43 | B44 | B45 |
| TAZ | Azeotropic drying under vacuum? | Yes | Yes | Yes | Yes | Yes |
| TBIC adding | Was used TBIC distilled? | No | No | No | No | No |
|  | Temperature inside the flask, °C. | 60 | 60 | 60 | 60 | 60 |
|  | Adding time, min | 30 | 30 | 30 | 30 | 30 |
| Molar excess of TBIC compared to TAZ |  | 30.00% | 30.00% | 28.00% | 33.00% | 22.01% |
| Time kept at 70° C., min |  | 5 | 5 | 5 | 5 | 5 |
| Time for cooling down until 50° C., min |  | 10 | 10 | 10 | 10 | 10 |
| Time for cooling down at 10° C., min |  | 120 | 120 | 120 | 120 | 120 |
| Amicarbazone purity, % w/w |  | 98.2% | 97.3% | 93.5% | 92.9% | 89.3% |

Poor quality - TBIC = 81.20% purity
Azeotropic drying of TAZ under vacuum = Yes
Was used TBIC distilled = No
Molar excess of TBIC compared to TAZ = More than 18%
Amicarbazone purity, % w/w = high purity

|  |  | Reactants |  |
|---|---|---|---|
| Reagents | Purity (%) | B46 | B47 |
| TBIC (Poor quality) | 81.20% | 29.1667 | 29.1667 |
| TBIC (Good quality) | 98.50% | — | — |
| TAZ | 97.71% | 34.1898 | 32.8769 |
| Toluene | 99.27% | 103.5673 | 103.5673 |
| KOH (51.81%) | 51.81% | 0.7777 | 0.7777 |
| Washing Water | — | 35.3582 | 35.3582 |
| moles TBIC |  | 0.294 | 0.294 |
| moles TAZ |  | 0.235 | 0.226 |
| Moles Ratio TBIZ/TAZ |  | 25.00% | 30.00% |
| TAZ | Azeotropic drying under vacuum? | Yes | Yes |
| TBIC adding | Was used TBIC distilled? | No | No |
|  | Temperature inside the flask, °C. | 60 | 60 |
|  | Adding time, min | 30 | 30 |
| Molar excess of TBIC compared to TAZ |  | 25.00% | 30.00% |
| Time kept at 70° C., min |  | 5 | 5 |
| Time for cooling down until 50° C., min |  | 10 | 10 |
| Time for cooling down at 10° C., min |  | 120 | 120 |
| Amicarbazone purity, % w/w |  | 92.0% | 96.1% |

Poor quality - TBIC = 81.20% purity
Azeotropic drying of TAZ under vacuum = Yes
Was used TBIC distilled = No
Molar excess of TBIC compared to TAZ = More than 18%
Amicarbazone purity, % w/w = high purity

|  |  | Reactants |  |  |  |
|---|---|---|---|---|---|
| Reagents | Purity (%) | B49 | B50 | B51 | B52 |
| TBIC (Poor quality) | 81.20% | 30.0000 | 30.0000 | 30.0000 | 30.0000 |
| TBIC (Good quality) | 98.50% | — | — | — | — |
| TAZ | 97.71% | 40.7013 | 38.2273 | 41.8644 | 41.8644 |
| Toluene | 99.27% | 106.5263 | 106.5263 | 106.5263 | 106.5263 |
| KOH (51,81%) | 51.81% | 0.7716 | 0.7716 | 0.7716 | 0.7716 |
| Washing Water | — | 36.3684 | 36.3684 | 36.3684 | 36.3684 |
| moles TBIC |  | 0.302 | 0.302 | 0.302 | 0.302 |
| moles TAZ |  | 0.280 | 0.263 | 0.288 | 0.288 |

|  |  | Reactants | | | |
| --- | --- | --- | --- | --- | --- |
| Reagents | Purity (%) | B49 | B50 | B51 | B52 |
| Moles Ratio TBIZ/TAZ | | 8.01% | 15.00% | 5.00% | 5.00% |
| TAZ | Azeotropic drying under vacuum? | Yes | Yes | Yes | Yes |
| TBIC adding | Was used TBIC distilled? | Yes | Yes | Yes | Yes |
| | Temperature inside the flask, ° C. | 60 | 60 | 60 | 60 |
| | Adding time, min | 30 | 30 | 30 | 30 |
| Molar excess of TBIC compared to TAZ | | 8.01% | 15.00% | 5.00% | 5.00% |
| Time kept at 70° C., min | | 5 | 5 | 5 | 5 |
| Time for cooling down until 50° C., min | | 10 | 10 | 10 | 10 |
| Time for cooling down at 10° C., min | | 120 | 120 | 120 | 120 |
| Amicarbazone purity, % w/w | | 95.5% | 82.6% | 82.6% | 87.8% |

Poor quality - TBIC = 81.20% purity
Azeotropic drying of TAZ under vacuum = Yes
Was used TBIC distilled = Yes
Molar excess of TBIC compared to TAZ = less than 18%
Amicarbazone purity, % w/w = low purity

|  |  | Reactants | | | |
| --- | --- | --- | --- | --- | --- |
| Reagents | Purity (%) | B54 | B55 | B57 | B58 |
| TBIC (Poor quality) | 81.20% | — | — | — | — |
| TBIC (Good quality) | 98.50% | 30.0000 | 30.0000 | 30.0000 | 30.0000 |
| TAZ | 97.71% | 42.2680 | 42.2680 | 42.2680 | 42.2680 |
| Toluene | 99.27% | 106.5263 | 106.5263 | 106.5263 | 106.5263 |
| KOH (51.81%) | 51.81% | 0.7716 | 0.7716 | 0.7716 | 0.7716 |
| Washing Water | — | 36.3684 | 36.3684 | 36.3684 | 36.3684 |
| moles TBIC | | 0.302 | 0.302 | 0.302 | 0.302 |
| moles TAZ | | 0.291 | 0.291 | 0.291 | 0.291 |
| Moles Ratio TBIZ/TAZ | | 4.00% | 4.00% | 4.00% | 4.00% |
| TAZ | Azeotropic drying under vacuum? | Yes | Yes | Yes | Yes |
| TBIC adding | Was used TBIC distilled? | No | No | No | No |
| | Temperature inside the flask, ° C. | 60 | 60 | 60 | 60 |
| | Adding time, min | 30 | 30 | 30 | 30 |
| Molar excess of TBIC compared to TAZ | | 4.00% | 4.00% | 4.00% | 4.00% |
| Time kept at 70° C., min | | 5 | 5 | 5 | 5 |
| Time for cooling down until 50° C., min | | 10 | 10 | 10 | 10 |
| Time for cooling down at 10° C., min | | 120 | 120 | 120 | 120 |

-continued

| Reagents | Purity (%) | Reactants B54 | B55 | B57 | B58 |
|---|---|---|---|---|---|
| Amicarbazone purity, % w/w | | 97.25% | 94.56% | 93.99% | 97.10% |

Good quality - TBIC = 98.50% purity
Azeotropic drying of TAZ under vacuum = Yes
Was used TBIC distilled = No
Molar excess of TBIC compared to TAZ = less than 18%
Amicarbazone purity, % w/w = high purity (Since Good quality of TBIC is used)

| Reagents | Purity (%) | Reactants B59 | B60 | B61 |
|---|---|---|---|---|
| TBIC (Poor quality) | 81.20% | — | — | — |
| TBIC (Good quality) | 98.50% | 30.0000 | 30.0000 | 30.0000 |
| TAZ | 97.71% | 42.2680 | 42.6780 | 41.8662 |
| Toluene | 99.27% | 106.5263 | 106.5263 | 106.5263 |
| KOH (51.81%) | 51.81% | 0.7716 | 0.7716 | 0.7716 |
| Washing Water | — | 36.3684 | 36.3684 | 36.3684 |
| moles TBIC | | 0.302 | 0.302 | 0.302 |
| moles TAZ | | 0.291 | 0.294 | 0.288 |
| Moles Ratio TBIZ/TAZ | | 4.00% | 3.00% | 5.00% |
| TAZ | Azeotropic drying under vacuum? | Yes | Yes | Yes |
| TBIC adding | Was used TBIC distilled? | No | No | No |
| | Temperature inside the flask, ° C. | 60 | 60 | 60 |
| | Adding time, min | 30 | 30 | 30 |
| Molar excess of TBIC compared to TAZ | | 4.00% | 3.00% | 5.00% |
| Time kept at 70° C., min | | 5 | 5 | 5 |
| Time for cooling down until 50° C., min | | 10 | 10 | 10 |
| Time for cooling down at 10° C., min | | 120 | 120 | 120 |
| Amicarbazone purity, % w/w | | 97.22% | 98.27% | 98.27% |

Good quality - TBIC = 98.50% purity
Azeotropic drying of TAZ under vacuum = Yes
Was used TBIC distilled = No
Molar excess of TBIC compared to TAZ = less than 18%
Amicarbazone purity, % w/w = high purity (Since Good quality of TBIC is used)

We claim:

1. A method for the preparation of Amicarbazone comprising reacting 4-Amino-2,4-dihydro-5-(1-methylethyl)-3H-1,2,4-triazol-3-one (TAZ) with tert-Butyl isocyanate (TBIC) having low purity to form Amicarbazone, wherein said low purity TBIC has a purity of less than or equal to 85%, and wherein 18% or more molar excess of TBIC with respect to TAZ is used.

2. The process according to claim 1, comprising:

a) preparing a solution of TAZ, potassium hydroxide, and toluene;

b) raising the temperature of the solution obtained in step (a) to the range of 50° C. to 70° C.;

c) adding the low purity TBIC without distillation to the solution of step (b);

d) heating the solution obtained in step c) at temperature in the range of 60° C. to 75° C.; and e) cooling the solution obtained in step (d) to form the Amicarbazone.

3. The process as claimed in claim 2, wherein the solution in step (e) is cooled to the temperature in the range of 40° C. to 50° C.

4. The process as claimed in claim 2, wherein the cooled solution of step e) is optionally seeded with Amicarbazone.

5. The process as claimed in claim 1, wherein the TBIC has a purity equal to or less than 80%.

6. The process as claimed in claim 1, wherein the molar excess of TBIC with respect to TAZ is in the range of 18% to 22%.

7. The process as claimed in claim 2, wherein the purity of Amicarbazone obtained in step (e) is more than 97%.

* * * * *